United States Patent [19]

Himmele et al.

[11] 4,409,402
[45] Oct. 11, 1983

[54] TERT.-BUTOXYBUTANALS, TERT.-BUTOXYBUTANOLS, BIS-TERT.-BUTOXYPENTANALS AND BIS-TERT.-BUTOXYPENTANOLS

[75] Inventors: Walter Himmele, Walldorf; Werner Hoffmann, Neuhofen, both of Fed. Rep. of Germany

[73] Assignee: BASF Aktiengesellschaft, Ludwigshafen, Fed. Rep. of Germany

[21] Appl. No.: 167,790

[22] Filed: Jul. 11, 1980

[30] Foreign Application Priority Data

Aug. 10, 1979 [DE] Fed. Rep. of Germany ....... 2932527

[51] Int. Cl.$^3$ .................... C07C 47/02; C07C 43/13; C07C 00/00
[52] U.S. Cl. ................................. 568/496; 568/603; 568/678; 568/599; 568/497; 568/602
[58] Field of Search .............. 568/451, 496, 599, 603, 568/678, 602, 497

[56] References Cited

U.S. PATENT DOCUMENTS

| | | | |
|---|---|---|---|
| 2,197,467 | 4/1940 | Evans et al. | 568/679 |
| 2,302,121 | 11/1944 | Harris | 568/679 |
| 3,676,500 | 7/1972 | Mantell et al. | 568/496 |
| 4,101,588 | 7/1978 | Nienburg et al. | 568/603 |
| 4,226,637 | 10/1980 | Linden et al. | 568/678 |
| 4,244,876 | 1/1981 | Warner | 568/603 |

OTHER PUBLICATIONS

Castro, "J. Organic Chemistry" vol. 26, pp. 4183–4184.

Primary Examiner—Werren B. Lone
Attorney, Agent, or Firm—John H. Shurtleff

[57] ABSTRACT

Tert.-butoxybutanals and tert.-butoxybutanols (I) and bis-tert.-butoxypentanals and bis-tert.-butoxypentanols (II)

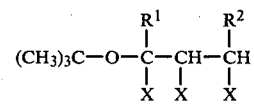

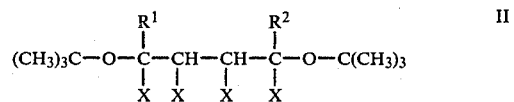

where $R^1$ and $R^2$ are H or $C_1$–$C_4$-alkyl, one X is —CHO or —CH$_2$OH and the others are H.

These compounds, which are valuable as fragrances and for use in organic syntheses are obtained by hydro-formylating the ethers (III) and bis-ethers (IV), respectively, using Rh catalysts.

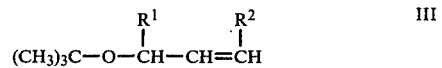

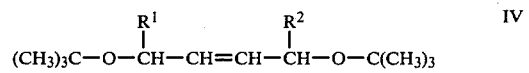

10 Claims, No Drawings

TERT.-BUTOXYBUTANALS, TERT.-BUTOXYBUTANOLS, BIS-TERT.-BUTOXYPENTANALS AND BIS-TERT.-BUTOXYPENTANOLS

The present invention relates to tert.-butoxybutanals and tert.-butoxybutanols, as well as to bis-tert.-butoxypentanals and bis-tert.-butoxypentanols, of the general formulae I and II We have found that the aldehyde-ethers IA and IIA may be obtained in a conventional manner by hydroformylating the corresponding allyl-ethers (III) or bis-ethers of but-2-ene-1,4-diols (IV)

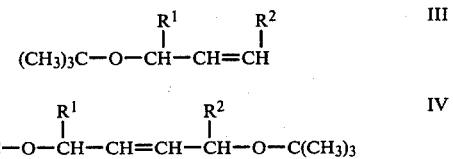

in the presence of a rhodium catalyst.

Depending on the reaction conditions and depending on whether $R^1$ and $R^2$ are hydrogen or alkyl, the hydroformylation of III and IV gives the various possible isomers of compounds of the general formulae IA and IIA, namely IA/a, IA/b, IA/c, IIA/a, IIA/a', IIA/b and IIA/b'.

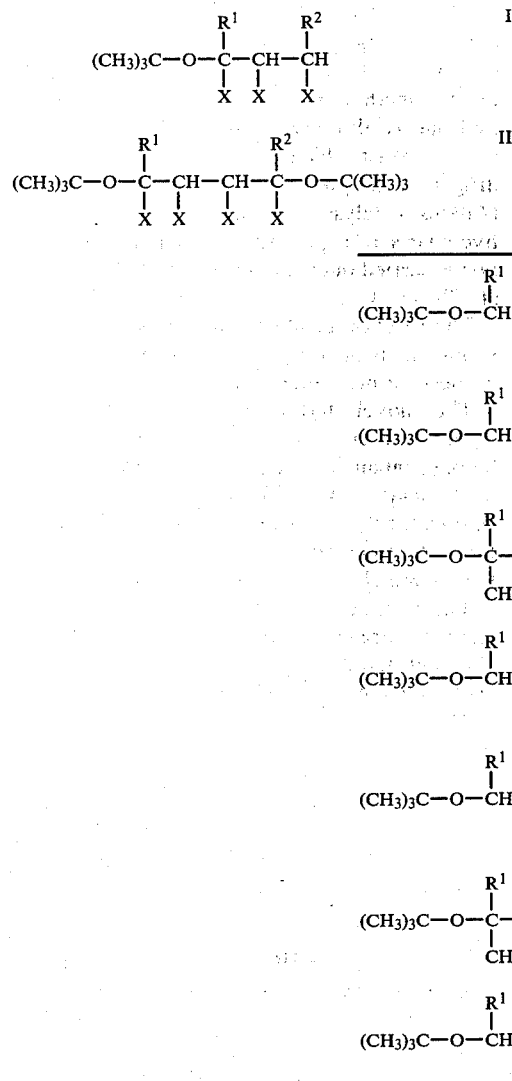

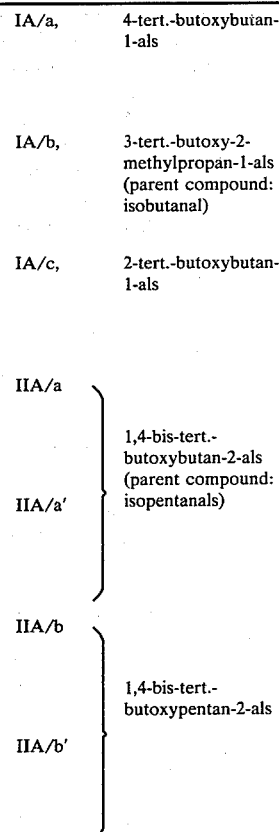

where $R^1$ and $R^2$ are hydrogen or $C_1$-$C_4$-alkyl, one of the radicals X is formyl or hydroxymethyl and the others are hydrogen.

The novel aldehydes, i.e. those compounds I and II where one of the radicals X is formyl, are hereafter referred to as compounds IA and IIA whilst the corresponding alcohols, where X is hydroxymethyl, are referred to as compounds IB and IIB.

It is an object of the invention to provide novel fragrances and novel intermediates for organic syntheses.

This object is achieved by providing the compounds of the general formulae I and II.

If, in a compound IA, the radicals $R^1$ and $R^2$ are hydrogen, as is the preferred case, reaction at 50–700 bar and 50°–100° C., for from 2 to 12 hours, using a catalyst concentration equivalent to 50–1,000 ppm of rhodium, expressed as metal and based on the amount of reaction mixture, gives isomer mixtures of compounds of type IA/a and IA/b in the ratio of about 70–30% to 45–55%, whilst the compound of type IA/c is only produced in minor amount. Under the same reaction conditions, and again with $R^1$ and $R^2$ being hydrogen, as is preferred, IV gives almost exclusively the compound of type IIA/a (=IIA/a', because of the symmetry of the compound), accompanied by minor amounts of the isomeric aldehyde of type IIA/b.

Higher or predominant proportions of the compounds of type IA/c and IIA/b are obtained, if $R^1$ and $R^2$ are hydrogen, by hydroformylating the starting olefins at 50–700 bar and 110°–160° C., with a reaction time of 0.5–6 hours and a catalyst concentration of 10–200 ppm of Rh. Under these conditions, intensified olefin isomerization of the type

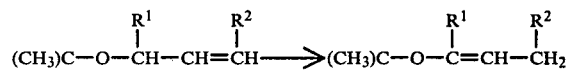

takes place. This isomerization can also be carried out separately, in a preliminary reaction using an isomerization catalyst at 100°–180° C., suitable isomerization catalysts being Pd and Cu as well as, preferably, rhodium compounds in concentrations of 50–1,000 ppm. The hydroformylation can subsequently be carried out under the conditions described for the preparation of the compounds of type IA/a, IA/b and IIA/a.

If one or two of the radicals $R^1$ and $R^2$ are alkyl, the reaction conditions for the preparation of the compounds IA/a, IA/b, IIA/a and IIA/a', on the one hand, and of the compounds IA/c, IIA/b and IIA/b' on the other hand, are as described for the unsubstituted compounds, but the isomer ratio is different, because of the influence of the substituents in accordance with Keulemans' rule, according to which the formyl group preferably attaches itself to those carbon atoms which still carry the largest number of H atoms and/or which suffer from least steric hindrance.

The starting compounds III and IV are known or may be obtained in a known manner by reacting the corresponding alcohols V and VI

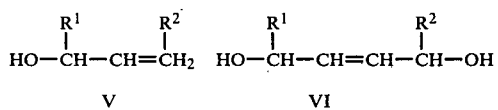

with isobutene in the presence of an acid catalyst. The most important parent compounds V and VI, from which the compounds I and II according to the invention may be derived, are allyl alcohol ($R^1=R^2=H$)
but-1-en-3-ol ($R^1=CH_3$; $R^2=H$)
but-2-en-1-ol ($R^1=H$; $R^2=CH_3$)
but-2-ene-1,4-diol ($R^1=R^2=H$)
pent-2-ene-1,4-diol ($R^1=H$; $R^2=CH_3$) and
hex-3-ene-2,4-diol ($R^1=R^2=CH_3$), and in the case of isomeric compounds the cis-form and trans-form are equally suitable.

Apart from the special hydroformylations referred to above and intended to control the isomer ratios, the hydroformylation is carried out in a conventional manner, in general at 200–700 bar and 80°–120° C., with a reaction time of 3–6 hours and a catalyst concentration of 50–250 ppm of Rh. Preferably, an equimolar or about equimolar mixture of carbon monoxide and hydrogen is employed. The presence of a solvent is not essential but is frequently advisable, for example in order to ensure that a homogeneous reaction medium is obtained. Examples of suitable solvents are diethyl ether, dioxane, tetrahydrofuran and aromatics, e.g. toluene and xylene.

Suitable catalysts are Rh complexes, e.g. $Rh_2(cyclooctadiene)_2Cl_2$, $Rh_2(ethylene)_2Cl_2$, $Rh_2(CO)_2Cl_2$ and $Rh_2(acetate)_4$.

Instead of using the complexes, other rhodium compounds, e.g. rhodium oxide or rhodium salts such as rhodium acetate may be employed, since the active carbonyl complexes form in situ under the reaction conditions, where relevant with participation of additional separately introduced ligands, such as triphenylphosphine.

If the compounds IA and IIA are hydrogenated, the corresponding ether-alcohols IB and IIB are obtained, in which the formyl group is in each case replaced by a hydroxymethyl group. The hydrogenation may be carried out by all conventional methods for such a reaction, amongst which catalytic hydrogenation with hydrogen in the presence of Raney nickel, Cr/Cu oxide (Adkins) catalysts or noble metal catalysts, e.g. Pt/active charcoal, is preferred. Preferably, the hydrogenation is carried out in methanol or ethanol as the solvent, at 20°–200° C. under a pressure of 1–200 bar.

The reaction products may be worked up in a conventional manner by fractional distillation, since the isomers formed differ in boiling point.

The novel tert.-butoxybutanals and tert.-butoxybutanols I, and bis-tert.-butoxypentanals and bis-tert.-butoxypentanols II are valuable fragrances having a fresh menthol-like to floral scent. They may therefore be used for the production of cosmetics of all kinds, and for perfuming detergents, cleansers and similar formulations and chemicals for domestic and commercial use.

The compounds I and II may also be used as intermediates for organic syntheses.

Direct derivatives of I and II to be mentioned especially are the aldehyde-alcohols and polyols VII and VIII

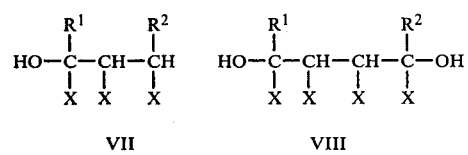

where one X is —CHO or —$CH_2OH$ and the others are H, these derivatives being obtained in a conventional manner by removing the tert.-butoxy group under acid catalysis.

One of the novel compounds, namely 2-methyl-3-tert.-butoxypropan-1-ol

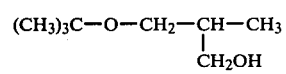

is an important intermediate for the synthesis of α-tocopherol by the method described in J. Org. Chem., 41 (1976), 3505.

This intermediate, which hitherto was obtained by reducing the tert.-butyl ether of β-hydroxyisobutyric acid with lithium alanate is now obtainable substantially more economically via the novel 2-methyl-3-tert.-butoxypropan-1-al.

EXAMPLE 1

4-tert.-Butoxybutan-1-al and 2-methyl-3-tert.-butoxypropan-1-al 1,800 g of allyl tert.-butyl ether were hydroformylated in a conventional manner with an equimolar mixture of CO and H$_2$ and 250 mg of dirhodium-dicyclooctadiene dichloride, in the presence of 2,000 g of tetrahydrofuran, by reaction at 70° C. and 650 bar for 24 hours.

According to analysis by gas chromatography, the reaction mixture contained 911 g of 4-tert.-butoxybutan-1-al and 1,097 g of 2-methyl-3-tert.-butoxypropan-1-al. This corresponds to yields of 41% and 49% respectively, and to an isomer ratio of about 45:55.

Fractional distillation of the reaction mixture, after removal of the solvent, through a column packed with stainless steel gauze spirals gave the pure aldehydes, namely:

4-tert.-Butoxybutan-1-al, boiling point 76°–77° C./32 mbar; refractive index $n_D^{20}$ 1.4149; scent: sweet, floral.

2-Methyl-3-tert.-butoxypropan-1-al, boiling point 69°–70° C./32 mbar; refractive index $n_D^{20}$ 1.4129; scent: floral, fatty, green, aldehyde-like.

EXAMPLE 2

4-tert.-Butoxybutan-1-al, 2-methyl-3-tert.-butoxypropan-1-al and 2-tert.-butoxybutan-1-al 4,100 g of allyl tert.-butyl ether were reacted with an equimolar mixture of CO and H$_2$ and 50 mg of the Rh catalyst used in Example 1 at 130° C. and 200 bar for 12 hours.

The volatile constituents of the reaction mixture were then distilled off under 50 mbar, leaving the catalyst and solid and high-boiling residues; 1,210 g of residue and 3,480 g of distillate were obtained. Since the allyl ether was no longer detectable, the conversion is calculated, as a first approximation, to be about 74%. According to analysis by gas chromatography, the yield, based on material converted (=100%) was 16% of 4-tert.-butoxybutan-1-al,
32% of 2-methyl-3-tert.-butoxypropan-1-al and
30% of 2-tert.-butoxybutan-1-al.

The remainder consisted of substances not identified further.

Fractional distillation gave the three isomeric tert.-butoxybutanals in about the same yields as those indicated by gas-chromatographic analysis.

2-tert.-Butoxybutan-1-al has the following properties: boiling point 47° C./14 mbar; $n_D^{20}$ 1.3977; scent: sour and pungent; herbal after 2 hours.

EXAMPLE 3

4-tert.-Butoxypentan-1-al and 2-methyl-3-tert.-butoxybutan-1-al 3,500 g of 3-tert.-butoxybut-1-ene were hydroformylated in a conventional manner, using an equimolar mixture of CO and H$_2$ and 250 mg of the Rh catalyst mentioned in Example 1, for 36 hours at 60° C. and 650 bar.

Working up the reaction by distillation gave the following:

4-tert.-Butoxypentan-1-al; boiling point 73° C./14 mbar; $n_D^{20}$ 1.4242; scent: fatty, herbal 2-Methyl-3-tert.-butoxybutan-1-al; boiling point 67° C./14 mbar; $n_D^{20}$ 1.4186; scent: floral, sweetish.

EXAMPLE 4

2-Formyl-1,4-bis-tert.-butoxybutane 2,500 g of 1,4-bis-tert.-butoxybut-2-ene were hydroformylated in a conventional manner by means of an equimolar mixture of CO and H$_2$ and 50 mg of the Rh catalyst mentioned in Example 1, in the presence of 2,000 g of tetrahydrofuran, at 100° C. and 650 bar for 24 hours.

Fractional distillation of the reaction mixture gave the above aldehyde-bis-ether in an absolute yield of 79%. Boiling point 77°–78° C./5 mbar.

EXAMPLE 5

3-Formyl-2,5-bis-tert.-butoxyhexane 200 g of 2,5-bis-tert.-butoxyhex-3-ene were hydroformylated in a conventional manner by means of an equimolar mixture of CO and H$_2$ and 100 mg of the Rh catalyst mentioned in Example 1, in the presence of 200 g of toluene, at 70° C. and 650 bar for 12 hours. Fractional distillation of the reaction mixture gave the above aldehyde-bis-ether. Boiling point (with slight decomposition) 135°–145° C./4 mbar.

EXAMPLE 6

4-tert.-Butoxynonan-1-al and 2-methyl-3-tert.-butoxyoctan-1-al 200 g portions of 3-tert.-butoxyoct-1-ene were hydroformylated in a conventional manner by means of an equimolar mixture of CO and H$_2$ and 100 mg of the Rh catalyst mentioned in Example 1, in the presence of 200 g of tetrahydrofuran, at 650 bar for 12 hours, (a) at 80° C. or
(b) at 110° C.

The conversion of the starting compound, determined by gas chromatography, was 84% at 80° C. and 91% at 110° C. Conventional working up of the reaction mixtures gave the following results:

4-tert.-Butoxynonan-1-al; absolute yield at 80° C.: 45%; absolute yield at 110° C.: 61%; boiling point: 74° C./0.5 mbar; $n_D^{20}$ 1.4350; scent: floral, jasmine-like even after 24 hours.

2-Methyl-3-tert.-butoxyoctan-1-al; absolute yield at 80° C.: 28%; absolute yield at 110° C.: 29%; boiling point: 95°–96° C./13 mbar; scent: fatty.

EXAMPLE 7

2-tert.-Butoxybutan-1-ol

A suspension of 250 g of ethanol and 30 g of a Cu/Cr oxide hydrogenation catalyst (Adkins catalyst) was initially heated for 12 hours at 120° C. under a hydrogen pressure of 100 bar, in order to activate the catalyst.

Thereafter, 438 g of 2-tert.-butoxybutanal were added to the above suspension at 80° C. and 60 bar in the course of 6 hours, after which the mixture was left to react under the same conditions for a further 12 hours.

On conventional working up after removal of the catalyst, the reaction mixture gave the compound shown in the heading. Yield: 83%. Boiling point 108° C./100 mbar; $n_D^{20}$ 1.4249; scent: menthol-like, minty.

EXAMPLE 8

2-Methyl-3-tert.-butoxypropan-1-ol

This compound was prepared from 2-methyl-3-tert.-butoxypropanal by the method described in Example 7.

Yield: 88%; boiling point 71° C./15 mbar; scent: menthol-like, floral.

EXAMPLE 9

4-tert.-Butoxybutan-1-ol

This compound was prepared from 4-tert.-butoxybutan-1-al by the method described in Example 7.

Yield: 78%; boiling point: 86° C./14 mbar; $n_D^{20}$ 1.4269; scent: floral, suggestive of linalool.

We claim:

1. A compound of one of the formulae:

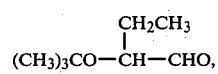

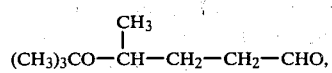

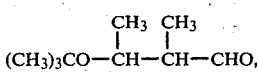

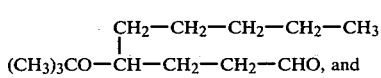

-continued

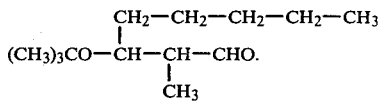

2. A compound as claimed in claim 1 which is 2-tert.-butoxybutan-1-al.

3. A compound as claimed in claim 1 which is 4-tert.-butoxypentan-1-al.

4. A compound as claimed in claim 1 which is 2-methyl-3-tert.-butoxybutan-1-al.

5. A compound as claimed in claim 1 which is 4-tert.-butoxynonan-1-al.

6. A compound as claimed in claim 1 which is 2-methyl-3-tert.-butoxyoctan-1-al.

7. A compound of the formula

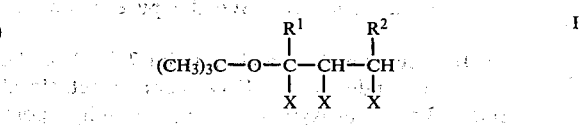

wherein $R^1$ and $R^2$ are hydrogen or $C_1$- to $C_4$-alkyl, one of X is hydroxymethyl and the others are hydrogen.

8. A compound as claimed in claim 7 which is 2-tert.-butoxybutan-1-ol.

9. A compound as claimed in claim 7 which is 2-methyl-3-tert.-butoxypropan-1-ol.

10. A compound as claimed in claim 7 which is 4-tert.-butoxybutan-1-ol.

* * * * *